United States Patent [19]

Ramsey

[11] Patent Number: 5,206,179
[45] Date of Patent: Apr. 27, 1993

[54] FLUORESCENCE POLARIZATION IMMUNOASSAYS FOR MULTIPLE ANALYTES USING SEQUENTIAL ADDITION OF TRACERS

[75] Inventor: Jack F. Ramsey, Lewisville, Tex.

[73] Assignee: Abbott Laboratories, Abbott Park, Ill.

[21] Appl. No.: 674,803

[22] Filed: Mar. 25, 1991

[51] Int. Cl.$^5$ ............................................. G01N 33/542
[52] U.S. Cl. .................................. 436/537; 364/497;
 435/973; 436/805; 436/815; 436/816; 436/817
[58] Field of Search ............... 436/536, 537, 546, 800,
 436/805, 815–818; 435/973; 364/497–499

[56] References Cited

U.S. PATENT DOCUMENTS 4,778,751 10/1988 El Shami et al. ............... 436/538 X
4,863,876 9/1989 Hevey ............................. 436/822 X

OTHER PUBLICATIONS

David B. Gordon, "Measurement of Angiotensinogen in Human Serum by Fluorescence Polarization Immunossay" Clin. and Exper. Hyper. Theory and Practice, A10(3), 485–503 (1988).

D. L. Colbert and M. Childerstone, "Multiple Drugs of Abuse in Urine Detected with a Single Reagent and Fluorescence Polarization"–Clin. Chem. 33/10 1921–1923 (1987).

Frank V. Bright and Linda B. McGown, "Homogeneous Immunoassay of Phenobarbital by Phase-Resolved Fluorescence Spectroscopy"–Talanta, vol. 32, No. 1, pp. 15–18, 1985.

Mohammad H. H. Al-Hakiem, D. S. Smith and J. Landon, "Development of Fluoroimmunoassay for the Determination of Individual or Combined Levels of Procainamide and N-Acetylprocainamide in Serum"–Journal of Immunoassay, 3(1), 91–110 (1982).

A. T. M. Al-Ani, M. H. H. Al-Hakiem and T. Chard, "Sequential Fluoroimmunoassay for Measurement of Pregnancy Specific B, Glycoprotein Using Antibody Coupled to Magnetisable Particles"–Clinica Chemica Acta, 112 (1981) 91–98.

Primary Examiner—Robert J. Hill, Jr.
Attorney, Agent, or Firm—Thomas M. Breininger

[57] ABSTRACT

A methodology is presented which relates in general to fluorescence polarization immunoassays (FPIA) and modifications of current processes wherein detection and quantification of several commonly abused or therapeutic drugs in a single biological fluid sample are determined utilizing manual or current software or related equipment to allow the sequential and simultaneous performance of more than one FPIA assay. The methodology involves combining the reagents either separately or pre-mixed, for multiple assays in a single reagent package, these reagents being used to assay quantitative amounts of each of the assay analytes in a sequential step manner. The assay being performed by mixing the sample with a combination reagent and then initiating a specific reaction for each of the separate analytes by sequentially adding a specific reagent, i.e. tracer for each and reading the results during each separate stage to determine the specific reaction taken place and utilization of manual or software modification monitoring to subtract out the contribution to total signal of each specific reagent added previously to the stage of interest.

11 Claims, No Drawings

FLUORESCENCE POLARIZATION IMMUNOASSAYS FOR MULTIPLE ANALYTES USING SEQUENTIAL ADDITION OF TRACERS

BACKGROUND OF THE INVENTION

This invention relates in general to fluorescence polarization immunoassays (FPIA) and modifications of current processes for detection of several commonly abused drugs in biological fluid wherein sequential or simultaneous performance of more than one FPIA assay is achieved utilizing a single cuvette. Combination of FPIA reagents and manual or software technologies allows for performance of at least two FPIA assays per cuvette. In another aspect, the invention relates to combination FPIA on analytes other than abused drugs.

Description of the Prior Art

Nonisotopic immunoassays widely used in clinical and research arenas for the determination of both the presence and the quantity of analytes such as proteins, nucleotide sequences, drugs, steroids and the like can be divided into two types: heterogeneous assays and homogeneous assays.

The heterogeneous assays utilize for example, a solid support such as beads in order to bind labeled reagents to the support while the remainder of the reagents remains unbound. A procedure is required to separate bound and free labeled reagents. In homogeneous assays, no separation is required, thus eliminating the need for an additional step. There are at least five types of homogeneous immunoassays routinely used. One of these, fluorescence polarization immunoassays (FPIA), can be used to measure small quantities of substances for example, in a nanogram-per-milliliter range. Use is made of the fact that molecules can exist in a ground or low energy state and, after exposure to incident radiation, an excited or high energy state. Absorption of energy from this source results in promotion of one or more electrons in a molecule to higher energy levels. As this jump occurs, the electron may lose a small percentage of the absorbed energy, for example, collisions with other molecules and the like. As its electrons return from higher energy levels to ground state, the excited molecule can radiate energy. The energy generated in this way is, however, less than that ordinarily involved in exciting the molecule. As a result, the wavelength of the light emitted, fluorescence light, is longer than that of the light used to excite the molecule. Emitted light energy can be detected using standard equipment, such as a detector positioned at a right angle to the incident light beam.

Understanding of FPIA also requires understanding of polarized light. Ordinary light can be thought of as a number of electromagnetic waves, each in a single plane; each wave passes through the central axis or path of the light beam. Polarized light, however, is light in which only one wave plane occurs (the others having been eliminated or screened out). When a fluorescence molecule is orientated such that its dipoles lie in the same plane as the light waves, it absorbs the polarized light. As it returns to its ground state, the molecule emits light in the same plane. Two additional factors of importance in FPIA are time related. First, the fluorescence lifetime of the molecule being used must be considered. The lifetime is the interval between excitation of the molecule by a polarized light burst and emission by the molecule of a similar burst. Second, the rotational relaxation time of the molecule, the time necessary for an excited molecule to move out of alignment so that the emitted polarized light is emitted in a direction different from its excitation must be taken into account. Small molecules rotate rapidly in solution; their rotational relaxation times are shorter than molecular fluorescence lifetime. As a result, after having absorbed polarized light, such small molecules become randomly orientated by the time a burst of polarized emitted light is obtained. Larger molecules, for example immunoglobulins, rotate relatively slowly and have rotational times longer than the typical fluorescence lifetime. Fluorescence polarization measurements rely on the fact that the polarized excitation radiation gives rise to polarized emission radiation if no molecular rotation of the fluorophore occurs. A fluorophore is a fluorescence molecule or a compound which has the property of absorbing light at one wave length and emitting it at a longer wave length. As described above, the fluorophore bound to a small molecule experiences molecular rotation at a rate that is rapid compared to the lifetime of the excited state prior to emission. Thus, the light is depolarized when bound to a small molecule. When antibody binds the fluorophore-antigen, rotation decreases dramatically because of the large size of the antibody, causing the emitted light to remain polarized.

This phenomenon is utilized in immunoassays, for example, with antibody and fluorophore-labeled hapten or fluorophore-labeled antigen present, binding occurs between antibody and fluorophore hapten or between antibody and fluorophore-antigen and total fluorescence polarization occurs. As antigen to be analyzed is added, the antigen binds to antibody competitively, fluorophore-antigen is not bound and depolarization is observed. The depolarization is a function of antigen concentration and constitutes a quantitative assay.

Methods exist which are useful for detection of specific antigens, i.e. substances whose introduction into an animal stimulates the production of antibodies capable of reacting specifically with the antigens. Competitive binding immunoassays are used for measuring ligands in a test sample. For purposes of this disclosure, a "ligand" is a substance of biological interest to be determined quantitatively by a competitive binding immunoassay technique. The ligands compete with a labeled reagent or ligand analog, or tracer, for a limited number of receptor binding sites on antibodies specific to the ligand and ligand analog. In recent years, such methods have become of utmost importance in both research and clinical environments involving the detection of specific antigens in biological fluids such as blood, sputum, urine and the like. The detection of antigens or antibodies capable of specifically combining can often be related to various disease states and consequently is extremely useful in diagnosis, in gaining basic understanding concerning the genus of the disease, and in monitoring the effectiveness of therapies. Many schemes for detecting ligands or anti-ligands have evolved over recent years based on the selective, immunological reactivity which characterizes these substances. Generally, these schemes are collectively termed immunoassays. The class of immunoassays discussed measure changes in fluorescence polarization and depolarization for the detection of ligands, in particular, the fluorescence depolarization methods have become most useful in connection with therapeutic drug and abused drug monitoring.

In such fluorescence depolarization immunoassay, the observation of a decrease in depolarization indicates increased binding of anti-ligand to the fluorescencely labeled ligand since such a binding results in a large molecule which rotates slowly and is thus, a less efficient depolarizing agent. If, on the other hand, the sample contains ligands which compete with the fluorescencely labeled ligands for binding sites on the anti-ligand, then fewer anti-ligand molecules are available to bind the fluorescencely labeled ligands and an increasing level of depolarization is observed. As may be readily appreciated, quantitation of such an assay may be conveniently accomplished using standard preparations for comparisons of samples containing known levels of the ligand. In fact, this technique is currently being used by Abbott Laboratories in its commercially available TDx ® instrument such as described in U.S. Pat. Nos. 4,269,511 and 4,420,568.

FPIA procedures have traditionally been limited to or directed to single analyte studies, however, more recently for example, multiple drug urine studies have been approached with a single reagent and fluorescent polarization process. The single reagent used, prepared by mixing four different antisera and three fluorescein-labeled derivatives, produced a polarized signal that is the average of the individual signals of the derivatives. The urine sample is added to the premixed reagent, incubated at room temperature for a few minutes, then fluorescence polarization is measured. The presence of any of several abused drugs at concentrations of one mg/L or more noticeably decreases the signal. Although other combinations are possible, the assay detects the presence of cocaine metabolite, amphetamine, and(or) several barbiturates.

Urines are screened for abused drugs by quantitative techniques followed if necessary, by a confirmatory assay. Among the screening techniques developed are radioimmunoassays involving separation, and non-separation enzymoimmunoassays. Rapid, easily automated assays are desirable and, for simplicity, several investigators have attempted to develop combination assays capable of detecting any one of several abused drugs. The use of fluorescence polarization immunoassays (FPIA) for individual drugs of abuse is well established. More recently, the use of a combination reagent capable of detecting benzoylecgonine (a cocaine metabolite), amphetamine, and several commonly abused barbiturates in urine has been published. The use of a single assay tube to detect the presence of one or more of several drugs simplifies the initial screening procedure and reduces cost. Such a mixture approach i.e., four different antiserum and three different fluorescein-labeled derivatives, provides a reaction soup which may detect the presence of more than one of several drugs. However, it does not detect or quantify the amount of each drug once the drug presence is known.

Other single analyte fluorescence polarization immunoassay methodology is utilized in, for example, the analyte digoxin in a biological fluid. Digoxin is a potent cardiac glycoside widely prescribed for the treatment of patients suffering from congestive heart failure as well as from some types of cardiac arrhythmias. Digoxin toxicity is a common and serious problem in a clinical setting.

As previously mentioned, the methodology of FPIA for measuring the concentration of drugs or other analytes in biological fluids such as human serum or plasma is well known. Fully-automated assays can be used in conjunction with an analytical instrument such as the TDx ® analyzer available from Abbott Laboratories, Abbott Park, Ill. The TDx ® is suitable as a batch analyzer utilizing one reagent set per run while the ADx ® has the ability to utilize multiple reagent sets per run. Both the TDx ® and the ADx ® provide suitable analyzer technology for use according to the invention. Following, is a full discussion of such an assay for the analyte digoxin; however, the TDx ® procedures are suitable for use in the combination fluorescence polarization immunoassays method of the present invention.

ANALYTE CALIBRATION

An art taught FPIA system utilizing the TDx ® is presented in the following discussion to more clearly focus on FPIA and microprocessor controlled testing using the FPIA system for the assay of the analyte digoxin. Controls and a series of human serum samples containing unknown digoxin levels were prepared. A centrifuge tube was designated for each sample to be tested, and placed in a suitable rack. A pipettor was filled with the precipitation reagent prepared as previously described in this example, and 200 microliters of the reagent were dispensed into each centrifuge tube by touching the tip of the pipettor to the wall of the centrifuge tube and depressing the dispensing button on the pipettor. Then, 200 microliters of each serum sample were pipetted into its corresponding centrifuge tube containing the precipitation reagent. After pipetting of the samples, each centrifuge tube was capped and mixed on a vortex mixer for 3-5 seconds, to ensure thorough mixing. The tubes were then placed into a centrifuge head, and centrifuged for about ninety (90) seconds at 9.500×g, until a clear supernatant and a hard compact pellet of denatured protein was obtained. After centrifugation was complete, each tube was uncapped and 250 microliters of the supernatant decanted into the corresponding sample well of a TDx ® Sample Cartridge (commercially available from Abbott Laboratories;, in preparation for performing the digoxin assay. The remainder of the digoxin assay procedure was performed substantially as a routine assay or calibration run on the TDx ® Analyzer. In this regard, reference is made to the "Procedures for Operation" section of the "TDx ® System Operation" manual, previously described, for further details of the protocol used. The following is a description of the major aspects of the performance of the assay.

ASSAY OPERATION

All assay steps are controlled by the microprocessor and protocols programmed into the software of a TDx ® Analyzer. A specific pattern on a barcode label is scanned by a barcode reader and the corresponding protocol is retrieved from the computer memory of the Analyzer. Each protocol contains detailed instructions for movement of pipetting syringes of the Analyzer which determines the volume of sample and reagents used in the pipetting steps, instruction for movement of a boom arm containing an aspirating probe, and for movement of a rotating carousel containing reaction cuvettes, as well as calibrator concentrations used for a calibration curve. The carousel has a unique barcode and set of instructions. Stepper motors, directed by an internal computer, move the carousel, syringes and boom arm. A light beam, focused on the carousel and controlled by the microprocessor, is used to monitor the number and placement of reaction cuvettes as the carousel rotates past. Two electrodes attached near the end of the probe serve as a liquid sensor which determines the presence of a liquid by electrical conductivity, thereby minimizing penetration of the probe into the samples and reagents.

The TDx® Analyzer automatically pipettes reagents and test samples while simultaneously pipetting dilution buffer, then dispenses both into a reaction cuvette positioned in a rotating carousel. Two pipetting syringes are driven down and the sample or reagent is aspirated at the same time the buffer is being drawn. When both syringes have been filled with the correct volumes, a boom arm moves the probe to the reaction cuvette, and the syringes are driven up, expelling their volumes. The liquids are dispensed at a high velocity creating sufficient turbulence for complete mixing.

Pipetting operations are performed with a dual syringe pump in conjunction with a boom assembly. A 250 microliter syringe is used to aspirate the sample and reagent, and a 2500 microliter syringe dispenses dilution buffer. The syringes are driven by two stepper motors which are computer-controlled for precise pipetting as determined by the assay parameters. The boom assembly consists of an arm which moves vertically and horizontally, teflon tubing which is integral with the probe and liquid level sensor, and a separate barcode reader which moves horizontally with the boom arm. For aspiration of samples or reagents, the boom arm moves in a horizontal arc until the probe is positioned over the proper sample cartridge well. The probe is then moved vertically until the tip comes in contact with the liquid and sample is aspirated. Upon completion of the aspiration, the boom moves up and horizontally, to position the probe over the dilution well or the cuvette. Coordinated rotation of the carousel occurs to bring a sample cartridge or cuvette into the correct position for receipt of the dispensed liquid.

The dilution buffer rests on a platform controlled by a microswitch which signals when the buffer is empty. Teflon tubing connects the buffer bottle to a valve block, liquid heater and boom arm. An integral valve directs the flow of liquids in and out of the syringe and tubing.

Some biological fluids, such as patient blood sera, evidence substantial background fluorescence which must be taken into consideration in order to obtain an accurate measurement of the analyte level in the sample. In the TDx® Analyzer, a sample blank for each sample, calibrator or control is automatically made and read before a fluorescence tracer is added to the reaction mixture in each cuvette. To obtain an indication of the true background fluorescence present in the final sample, the mixture on the first reading must be at the final diluted concentration. This is accomplished by adding half the sample volume to a reaction mixture representing half the final reaction mixture. The blank mixtures are measured by the fluorescence detector and the intensities are stored in the computer memory of the instrument.

After the remaining reagents and the rest of the sample are added and incubated, the final reading is made. The blank intensities are subtracted from the final reaction mixture intensities before polarization values are calculated by the TDx® Analyzer. The polarization equation becomes as follows:

$$P = \frac{(I_{vv} \text{ final} - I_{vv} \text{ blank}) - (I_{hv} \text{ final} - I_{hv} \text{ blank})}{(I_{vv} \text{ final} - I_{vv} \text{ blank}) + (I_{hv} \text{ final} - I_{hv} \text{ blank})}$$

The net and blank intensity for each cuvette is also calculated and printed, using the equation $$I_{Net} \text{ or } I_{Blk}) = 2I_{hv} + I_{vv}$$

MEASURING FLUORESCENCE POLARIZATION

The light source (excitation beam) used for the tungsten fluorescence polarization reading on the TDx® Analyzer is a halogen lamp. The light passes through a filter which selects the correct excitation wavelength (usually 485 nanometers), and a reference detector signal is used to monitor the intensity of the lamp. The computer of the instrument can adjust the lamp intensity to provide a constant and accurate measure of the background intensity of samples with naturally fluorescing substances. A liquid crystal-polarizer combination in the light path rapidly polarizes the excitation beam horizontally and then vertically many times in sequence for each reaction cuvette measured. The polarized excitation beam is focused with a lens into the center of the sample, in the reaction cuvette of the carousel. Baffles bordering the cuvette serve as light traps preventing the excitation beam from entering the emission optics (polarization detection means of the instrument. The light path for the emission optics is at a 75 degree angle to the excitation light path. Another lens collimates emitted light and passes it through an emission filter which selects light of a wavelength corresponding, e.g., to the emission peak of fluorescein (525-550 nanometers). Emitted light is then passed through a vertical polarizer, and a photomultiplier tube converts the fluorescence into an electrical current which is recorded as numbers to be entered into the polarization equation by the computerized electronics of the instrument, providing a polarization value for each reaction cuvette measured.

CALCULATION OF ANALYTE CONCENTRATION

The calibration curve for each assay is stored in permanent computer memory of the TDx® Analyzer. The stored curve equation is generated by assaying samples with increasing concentrations of the analyte and measuring the polarization value for each concentration. The appropriate data reduction for that assay calculates a best-fit curve equation using six calibrator concentrations, one of which is zero. Curve parameters of slope, span of polarization value between high and low calibrators, and polarization value of the zero calibrator are used to determine the best fit. Concentrations of the analyte in unknown samples are calculated from this curve equation using the polarization values generated for each sample in the assay.

Although the principle of FPIA has been known since the 1970's, and feasible instrumentation for the assay with automatic testing combined with microprocessing is available, multiple analyte and quantitative assays are only available by running separate reagents in separate cuvettes. The prior art disadvantage is based on through-put and disposable usage. None of the prior art deals with sequential FPIA with the obvious advantage of increasing efficiency of reagent and disposable use for clinics and laboratories along with cost savings and reduced packaging requirements. These advantages are achieved through a process for obtaining determinations of the presence or absence of multiple analytes as well as quantitative amounts in a single sample cuvette.

SUMMARY OF THE INVENTION

In accordance with the principles of the present invention, there is provided an accurate, relatively low cost and reliable methodology utilizing manual or current TDx®/ADx® FPIA reagent and software or related equipment to allow the sequential or simultaneous performance of more than one FPIA assay in a single cuvette. The process involves combining the reagents, either separately or premixed, for multiple assays in a single reagent package. These reagents are then used to assay quantitative amounts of each of the assay analytes in a sequential process. The assay is performed by mixing the sample with the combination reagent initially (i.e. mixture of antisera) and then initiating a specific reaction for each of the separate analytes by sequentially adding a specific reagent (i.e. tracer) for each and reading the results during each separate stage to determine the specific reaction taking place. Software modifications monitor and subtract out the contribution to total signal of each specific reagent added previously to the stage of interest.

DETAILED DESCRIPTION OF THE INVENTION

The combination FPIA will be presented in discussions of running two or more analytes in sequential process as well as the presentation of configurations of three analytes, although, theoretically the limit on the number of analytes achievable will be due only to constraints of reaction cuvette volume and mixing constraint=associated therewith.

Original combination FPIA according to the invention involved the mixing of equal parts of antiserum (S pot) reagents from two assays, cocaine and cannabinoids, to make the combo S reagent. A 4 pot R-pack was then constructed consisting of the combination S reagent, cocaine tracer (CocMT), cannabinoids tracer (CannbT), and the cannabinoids pretreatment (P pot). The sequence of the test is shown in the following Example I:

EXAMPLE I

The sample was mixed with the pretreatment in the predilute well and incubated. A portion of this mixture was transferred to the cuvette and a blank reading taken. The combo S reagent was added to the cuvette along with the CocMT reagent and the mixture was incubated. After the incubation, a reading was taken after which the cocaine metabolite concentration was calculated. The intensities from this reading were stored for use later. Another portion of the combo S reagent, the CannbT reagent and an additional portion of CocMT reagent were added to the cuvette and the mixture again incubated. After incubation a reading was taken and after correction for the value stored from the preceding reading, the cannabinoids concentration was calculated. The basic methodology of the FPIA and the estimation of concentrations from a stored calibration curve were identical to the current AD$_x$ TM technologies.

Following, is a description of the actual sequence of events utilized to perform a combination assay.
1) 25 microliters of sample and 25 microliters of a pretreatment solution were mixed together with 450 microliters of buffer in a predilution vessel.
2) 100 microliters of the diluted sample were transferred to the cuvette with 900 microliters of buffer.
3) Incubation for 30 seconds.
4) A reading was taken and stored.
5) 37.5 microliters of the combined antiserum reagent and 18.8 microliters of the first analyte (cocaine) tracer, along with 50 microliters of the diluted sample were added to the cuvette with 843.7 microliters of buffer.
6) Incubation for 420 seconds.
7) A second reading was taken and after correcting by the first reading, an mP value was calculated. The second reading was also stored.
8) 12.5 microliters of the combined antiserum reagent, 25 microliters of the second analyte (cannabinoids) tracer, 6.2 microliters of the first analyte tracer, and 50 microliters of the diluted sample were added to the cuvette along with 406.3 microliters of buffer.
9) Incubation for 300 seconds.
10) A third reading was taken and after correcting by the second reading, an mP value was calculated.

The data below is comprised of the mP values produced during two runs of the assay as previously described. The column labelled COC contains the mP calculated from the second readings for their respective cuvettes, and that labelled CANNB contains the mP calculated from the third readings. The readings were produced by the ADx® instrument having already been corrected by the first, or blank, reading. In run #1. the samples were 6 calibrators containing increasing concentrations of cocaine metabolite (benzoylecgonine). One can see the progressive lowering of the mP values for the 6 samples in the second or "COC" stage of the assay with little or no reaction in the third "cannab" stage. Conversely, for run #2 the samples are cannabinoid calibrators. One can see the lack of reaction in the second stage, while a progressive lowering of the mp values is seen in the third stage. This data demonstrates the selectivity of the assay technology.

| Sample | CONCENTRATIONS | COC | CANNB |
|---|---|---|---|
| | Run #1 | | |
| COC A | 0 ng/ml | 181.6 | 170.6 |
| COC B | 300 ng/ml | 134.0 | 169.3 |
| COC C | 1000 ng/ml | 101.6 | 164.0 |
| COC D | 2000 ng/ml | 84.8 | 165.6 |
| COC E | 3000 ng/ml | 74.5 | 160.8 |
| COC F | 5000 ng/ml | 64.8 | 164.1 |
| | Run #2 | | |
| CANNB A | 0 ng/ml | 180.3 | 166.5 |
| CANNB B | 25 ng/ml | 179.9 | 157.7 |
| CANNB C | 40 ng/ml | 179.2 | 143.6 |
| CANNB D | 60 ng/ml | 178.0 | 134.6 |
| CANNB E | 80 ng/ml | 178.6 | 122.6 |
| CANNB F | 150 ng/ml | 179.7 | 91.4 |

Representative of ligands determinable by the methods of the present invention include steroids such as estrone, estradiol, cortisol, testosterone, progesterone, digoxin, digitoxin, thyroxine, triiodothyronine, antiasthmatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepresant drugs including tricyclics such as nortriptyline, amitriptyline, imipramine and desipramine; and the like as well as the metabolites thereof.

Additional ligands that may be determined by the methods of the present invention include drugs of abuse such as morphine, heroin, hydromorphone, oxymorphone, codeine, hydrocodone, dextromethorphan, cannabinoids, various barbiturates, phencyclidine and and their metabolites and the like.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of a ligand, the observed polarization value is closer to that of the free ligand, i.e., low. In the test sample contains a low concentration of the ligand, the polarization value is closer to that of the bound ligand, i.e, high. By sequentially exciting the reaction mixture of an immunoassay with vertically and then horizontally polarized light and analyzing only the vertical component of the emitted light, the polarization of fluorescence in the reaction mix may be accurately determined. The precise relationship between polarization and concentration of the ligand to be determined is established by measuring the polarization values of calibrators with known concentrations. The concentration of the ligand can be extrapolated from a standard curve prepared in this manner.

In addition to the concentration range of the ligand of interest, considerations such as whether the assay is qualitative, semiquantitative or quantitative, the equipment employed, and the characteristics of the tracer and antibody will normally determine the concentration of the tracer and antibody to be employed. While the concentration of ligand and the sample will determine the range of concentration of the other reagents, i.e., tracer and antibody, normally to optimize the sensitivity of the assay, individual reagent concentrations will be determined empirically. Concentrations of the tracer and antibody are readily ascertained by one of ordinary skill in the art.

For purposes of presenting the combination FPIA invention for three analytes the following abbreviations will be utilized in the text:

$A_1$ = Analyte 1
$A_2$ = Analyte 2
$A_3$ = Analyte 3
] Various unknown quantities and/or combinations of these may be in a given sample.

$S_1$ = Antiserum to analyte 1
$S_2$ = Antiserum to analyte 2
$S_3$ = Antiserum to analyte 3
$S_1S_2S_3$ = Combined antiserum reagent -continued $T_1$ = Tracer for analyte 1
$T_2$ = Tracer for analyte 2
$T_3$ = Tracer for analyte 3
· = Denotes a bound pair (i.e., $S_1 \cdot T_1$)
mP = milli-Polarization, the unit of measure in FPIA
[ ] = As the equilibrium formulas become more involved, brackets will be used to delineate the analyte specific parts of the total reaction.

The following examples provide a description of the methodology according to the invention in stoichiometric terms:

EXAMPLE II: A NEGATIVE SAMPLE

Sample and combined antiserum are mixed and incubated. The resulting equilibrium is:

$$S_1S_2S_3 <-> S_1 + S_2 + S_3$$

After incubation, a reading is taken and stored as Blank Reading "B1"

$T_1$ is added and the mixture incubated. The resulting equilibrium is:

$$S_1 + S_2 + S_3 + T_1 <-> [S_1 + S_1 \cdot T_1 + T_1] + S_2 + S_3$$

After incubation, a reading is taken; "R1". This reading is corrected for "B1" and an mP value is calculated. In this scenario, the concentration of $S_1 \cdot T_1$ is high, therefore the mP value is high denoting no concentration of $A_1$ in the sample. The reading "R1" is then stored as "B2" $T_2$ is added and the mixture incubated. The resulting equilibrium is:

$$[S_1 + S_1 \cdot T_1 + T_1] + S_2 + S_3 + T_2 <-> \\ [S_1 + S_1 \cdot T_1 + T_1] + [S_2 + S_2 \cdot T_2 + T_2] + S_3$$

After incubation, a reading is taken; "R2". This reading is corrected for "B2", thus removing the fluorescence contribution of $T_1$ from the total, and an mP value is calculated. In this scenario, the concentration of $S_2 \cdot T_2$ is high, therefore the mP value is high denoting no concentration of $A_2$ in the sample. The reading "R2" is then stored as "B3" $T_3$ is added and the mixture incubated. The resulting equilibrium is $$[S_1 + S_1 \cdot T_1 + T_1] + [S_2 + S_2 \cdot T_2 + T_2] + \\ S_3 + T_3 <-> [S_1 + S_1 \cdot T_1 + T_1] + \\ [S_2 + S_2 \cdot T_2 + T_2] + [S_3 + S_3 \cdot T_3 + T_3]$$

After incubation, a reading is taken; "R3". This reading is corrected for "B3", thus removing the fluorescence contribution of $T_1$ an $T_2$ from the total, and an mP value is calculated. In this scenario, the concentration of $S_3 \cdot T_3$ is high, therefore the mP value is high denoting no concentration of $A_3$ in the sample.

EXAMPLE III: A SAMPLE CONTAINING ANALYTE 2 ONLY

Sample and combined antiserum are mixed and incubated. The resulting equilibrium is:

$$S_1S_2S_3 + A_2 = S_1 + [S_2 + S_2 \cdot A_2 + A_2] + S_3$$

After incubation, a reading is taken and stored as Blank Reading "B1" $T_1$ is added and the mixture incubated. The resulting equilibrium is:

$$S_1 + [S_2 + S_2 \cdot A_2 + A_2] + S_3 + T_1 <-> [S_1 + S_1 \cdot T_1 + T_1] + [S_2 + S_2 \cdot A_2 + A_2] + S_3$$

After incubation, a reading is taken; "R1". This reading is corrected for "B1" and an mP value is calculated. In this example, the concentration of $S_1 \cdot T_1$ is high, therefore the mP value is high denoting no concentration of $A_1$ in the sample. The reading "R1" is then stored as "B2" $T_2$ is added and the mixture incubated. The resulting equilibrium is:

$$[S_1 + S_1 \cdot T_1 + T_1] + [S_2 + S_2 \cdot A_2 + A_2] +$$
$$S_3 + T_2 <-> [S_1 + S_1 \cdot T_1 + T_1] +$$
$$[S_2 + S_2 \cdot A_2 + S_2 \cdot T_2 + A_2 + T_2] + S_2$$

After incubation, a reading is taken; "R2". This reading is corrected for "B2", thus removing the fluorescence contribution of $T_1$ from the total, and an mP value is calculated. In this example, the concentration of $S_2 \cdot T_2$ has been lowered due to some of $S_2$ being bound to $A_2$, therefore the mP value is lowered denoting a concentration of $A_2$ present in the sample. The reading "R2" is then stored as "B3" $T_3$ is added and the mixture incubated. The resulting equilibrium is:

$$[S_1 + S_1 \cdot T_1 + T_1] + [S_2 + S_2 \cdot A_2 + S_2 \cdot T_2 + A_2 + T_2] + S_3 + T_3 <-> [S_1 + S_1 \cdot T_1 + T_1] + [S_2 + S_2 \cdot A_2 + S_2 \cdot T_2 + A_2 + T_2] + [S_3 + S_3 \cdot T_3 + T_3]$$

After incubation, a reading is taken; "R3". This reading is corrected for "B3", thus removing the fluorescence contribution of $T_1$ and $T_2$ from the total, and an mP value is calculated. In this example, the concentration of $S_3 \cdot T_3$ is high, therefore the mP value is high denoting no concentration of $A_3$ in the sample.

EXAMPLE IV: A SAMPLE CONTAINING ANALYTE 1 AND ANALYTE 3

Sample and combined antiserum are mixed and incubated. The resulting equilibrium is:

$$S_1 S_2 S_3 + A_1 + A_3 <-> [S_1 + S_1 \cdot A_1 + A_1] + S_2 + [S_3 + S_3 \cdot A_3 + A_3]$$

After incubation, a reading is taken and stored as Blank Reading "B1"

$T_1$ is added and the mixture incubated. The resulting equilibrium is:

$$[S_1 + S_1 \cdot A_1 + A_1] + S_2 +$$
$$[S_3 + S_3 \cdot A_3 + A_3] + T_1 <->$$
$$[S_1 + S_1 \cdot A_1 + S_1 \cdot T_1 + A_1 + T_1 +$$
$$+ S_2 + [S_3 S_3 \cdot A_3 + A_3]$$

After incubation, a reading is taken; "R1". This reading is corrected for "B1" and an mP value is calculated. In this scenario, the concentration of $S_1 \cdot T_1$ has been lowered due to some of $S_1$ being bound to $A_1$, therefore the mP value is lowered denoting a concentration of $A_1$ present in the sample.

The reading "R1" is then stored as "B2"

$T_2$ is added and the mixture incubated. The resulting equilibrium is:

$$[S_1 + S_1 \cdot A_1 + S_1 \cdot T_1 + A_1 + T_1] + S_2 + [S_3 + S_3 \cdot A_3 + A_3] + T_2 <-> [S_1 + S_1 \cdot A_1 + S_1 \cdot T_1 + A_1 + T_1] + [S_2 + S_2 \cdot T_2 + T_2] + [S_3 + S_3 \cdot A_3 + A_3]$$

After incubation, a reading is taken; "R2". This reading is corrected for "B2", thus removing the fluorescence contribution of $T_1$ from the total, and an mP value is calculated. In this example, the concentration value is high denoting no concentration of $A_2$ present in the sample. The reading "R2" is then stored as "B3"

$T_3$ is added and the mixture incubated. The resulting equilibrium is:

$$[S_1 + S_1 \cdot A_1 + S_1 \cdot T_1 + A_1 + T_1] + [S_2 + S_2 \cdot T_2 + T_2] + [S_3 + S_3 \cdot A_3 + A_3] + T_3 <-> [S_1 + S_1 \cdot A_1 + S_1 \cdot T_1 + A_1 + T_1] + [S_2 + S_2 \cdot T_2 + T_2] + [S_3 + S_3 \cdot A_3 + S_3 \cdot T_3 + A_3 + T_3]$$

After incubation, a reading is taken; "R3". This reading is corrected for "B3", us removing the fluorescence contribution of $T_1$ and $T_2$ from the total, and an mP value is calculated. In this example, the concentration of $S_3 \cdot T_3$ has been lowered due to some of $S_3$ being bound to $A_3$, therefore the mP value is lowered denoting a concentration of $A_3$ present in the sample.

Following, are actual constituents of reagents for use in Example II, III and IV for two separate reagent systems.

| | Constituents: | | |
|---|---|---|---|
| | AMPHETAMINE/METHAMPHETAMINE COCAINE METABOLITE CANNABINOIDS (ACC) | | |
| S | Antibody Pot | | |
| | Citrate diluent | 974.12 | mLs/Ltr |
| | AM/MT II Antibody Stock | 11.28 | mLs/Ltr |
| | Cocaine Metabolite Antibody Stock | 13.68 | mLs/Ltr |
| | Cannabinoids Antibody Stock | 0.92 | mLs/Ltr |
| | Riboflavin Binding Protein | 10.0 | gms/Ltr |
| | Citrate Diluent | | |
| | Citric Acid Anhydrous Powder | 19.2 | gm/Ltr |
| | Sodium Hydroxide Pellets | 11.6 | gm/Ltr |
| | Sodium Azide | 1.0 | gm/Ltr |
| | distilled water | 995.0 | gm/Ltr |
| T1 | AM/MT II Tracer Pot | | |
| | distilled water | 1.0 | Ltr/Ltr |
| | Sodium phosphate (monobasic) | 8.53 | gm/Ltr |
| | Sodium phosphate (tribasic) | 14.53 | gm/Ltr |
| | Bovine gamma globulin | 0.10 | gm/Ltr |
| | Sodium Azide | 1.05 | gm/Ltr |
| | Amphetamine/Methamphetamine II Fluorescein | | |
| T2 | Cocaine Metabolite Tracer Pot | | |
| | distilled water | 1.0 | Ltr/Ltr |
| | Tris Ultra Pure | 12.11 | gm/Ltr |
| | 6N HCl | 13.0 | ml/Ltr |
| | Bovine Gamma Globulin | 0.10 | gm/Ltr |
| | Sodium Azide | 1.00 | gm/Ltr |
| | Cholic Acid (Sodium Salt) | 100.0 | gm/Ltr |
| T3 | Cannabinoids - GS Tracer Pot | | |
| | distilled water | 1.0 | Ltr/Ltr |
| | Sodium phosphate (monobasic) | 8.53 | gm/Ltr |
| | Sodium phosphate (tribasic) | 14.53 | gm/Ltr |
| | Bovine Gamma Globulin | 0.10 | gm/Ltr |

-continued

| | Constituents: | |
|---|---|---|
| | Sodium Azide | 1.05 gm/Ltr |
| | Cholic Acid (Sodium Salt) | 50.0 gm/Ltr |
| | Cannabinoids - GS Fluorescein | |
| P | AM/MT II Pretreatment Pot | |
| | distilled water | 0.992 Ltr/Ltr |
| | Sodium Periodate | 42.78 gm/Ltr |
| W | Cannabinoids - GS Wash Pot | |
| | distilled water | 515.35 gm/Ltr |
| | Dimethyl Sulfoxide | 550.05 gm/Ltr |
| | Sodium Chloride | 4.50 gm/Ltr |
| | BARBITURATES PCP OPIATES (BPO) | |
| S1 | Antibody Pot | |
| | 0.5M Hepes Buffer | 979.92 mLs/Ltr |
| | Barbs II Antibody Stock | 15.80 mLs/Ltr |
| | PCP II Antibody Stock | 4.28 mLs/Ltr |
| | Riboflavin Binding Protein | 10.0 gms/Ltr |
| | 0.5M Hepes Buffer Diluent | |
| | distilled water | 1000. |
| | HEPES, Powder | 11.92 gm |
| | Ovalbumin | 10.0 gm |
| | Bovine Serum Albumin | 8.0 gm |
| | Sodium Azide | 1.0 gm |
| | Glycerol | 119.0 gm |
| | 6N Sodium Hydroxide | as required |
| S2 | Antibody Pot | |
| | OPIATES Antibody Diluent | 965.80 mLs/Ltr |
| | OPIATES Antibody STOCK | 4.20 mLs/Ltr |
| | Normal Sheep Serum containing 0.15 mg/ml Dextromethorphan | 30.0 mLs/Ltr |
| | OPIATES Antibody Diluent | |
| | distilled water | 1.0 LTR/LTR |
| | Ethylene Glycol (density = 1.114) | 20.0 mL/LTR |
| | Sodium Phosphate (tribasic) | 14.53 gm/LTR |
| | Bovine Gamma Globulin, Cohn FRACTION 2 | 0.10 gm/LTR |
| | Sodium Azide | 1.05 gm/LTR |
| | Sodium Phosphate (monobasic) | 8.53 gm/LTR |
| T1 | Barbiturates Tracer Pot | |
| | distilled water | 0.892 LTR/LTR |
| | Sodium Phosphate (dibasic) Heptahydrate | 26.80 gm/LTR |
| | 6N Sodium Hydroxide | 55.0 mL/LTR (approx) |
| | Bovine Gamma Globulin | 0.1 gm/LTR |
| | Sodium Azide | 1.00 gm/LTR |
| | 5-Sulfo-Salicylate | 50.0 gm/LTR |
| | Barbiturates Fluorescein | |
| T2 | PCP Tracer Pot | |
| | Tris Ultra Pure | 12.11 gm/LTR |
| | 6N HCl | 13.0 ml/LTR (approx) |
| | Bovine Gamma Globulin | 0.1 gm/LTR |
| | Sodium Azide | 1.00 gm/LTR |
| | distilled water | 1.00 LTR/LTR |
| | Cholic Acid, (Sodium Salt) | 100.0 gm/LTR |
| | 6N Hydrochloric Acid | As required |
| | 6N Sodium Hydroxide | As required |
| | Phencyclidine Fluorescein | |
| T3 | OPIATES Tracer Pot | |
| | distilled water | 0.965 LTR/LTR |
| | Citric Acid Anhydrous Powder | 9.6 gm/LTR |
| | Sodium Hydroxide Pellets | 21.8 gm/LTR |
| | Bovine Gamma Globulin | 0.1 gm/LTR |
| | Sodium Azide | 1.00 gm/LTR |
| | 5-Sulfo-Salicylate | 50.0 gm/LTR |
| | 6N Sodium Hydroxide | As required |
| | Opiates Fluorescein | |
| W | PCP II WASH POT | |
| | distilled water | 410.0 gm/LTR |
| | 1-Butanol | 81.0 gm/LTR |
| | Dimethylformamide | 472.0 gm/LTR |
| | Sodium Chloride | 4.5 gm/LTR |

The preceding provides a description of the inventive process in simple terms. In addition to the specific tracer added at each of the stages, quantities of the combined antiserum and the tracers from the previous stages must also be added to balance and maintain the various equilibria that are being established. Without the balancing additions of these previous reagents, the reagent concentrations would become progressively more dilute and the equilibria would shift from one stage to the next. This would cause a corresponding change to the mP of the previous tracer/antiserum component. An mP shift would be manifest in a change in the ratio of the horizontal and vertical readings contribution from that particular tracer and it could not then be back subtracted based on the previous reading's values. This is of major importance to the assay technology since, without the back subtraction, one cannot differentiate one tracer's contribution from another's as the second and third stage readings are taken.

The balancing additions of antiserum and tracer are determinable mathematically from the volumes of the reaction mixture and the previously added volumes for the respective reagents. In simple terms, maintain the concentration of each of the reagents in the cuvette throughout the assay time. This is true however, only when each stage of the reaction is allowed to continue to complete equilibrium. In reality, each stage of the reaction is read slightly before equilibrium is reached and the reaction continues after the reading is taken. This is not a problem when the concentration of the analytes in the sample tested are negative or at moderate levels. The reactions approach their equilibrium levels rapidly and are almost complete when the reading is taken. Therefore, there is very little change in the mP of the tracer/antiserum combination and thus, no problem with the back subtraction which is important to the next stage. However, if one of the analytes is present in the sample at a very high level, the reaction approaches its final equilibrium more slowly and there is more of a continuation of the mP change after the reading is taken. This causes the back subtraction of this reading from the reading at the next stage to be in error and affects the answer obtained. In some cases this results in sufficient error in the subsequent mP calculated to give a false answer.

It is this fact that requires a special optimization of the balancing additions of the reagents. Either of the antiserum or tracer reagents can be adjusted to effect the equilibrium, or position relative to the reaction. It has been chosen to keep the concentration of the combined antiserum reagent at the mathematically determined level and utilize the separate tracer reagents to modulate the reactions relative to equilibrium. It has been determined experimentally that adding less than the calculated volume of the balancing addition of the tracers at subsequent stages reduces to acceptable levels, or eliminates, the interferences caused by very high analyte concentrations. Based on the data it has been found that by adding differing volumes of the balancing tracer additions it is possible to change either or both of the previous and subsequent reactions in such a way that the mP obtained in the second or third stage of the assay is not affected by, or is affected to only a slight degree, by the concentration of the analytes reacting in the previous stages.

EXAMPLE V

The following is a presentation of actual data of the optimization of the balancing sips of tracers for a typical Combination FPIA assay in accordance with Examples II, III, or IV. The assay in this example is designed to test sequentially for Barbiturates, Phencyclidine, and Opiates. The optimization is performed in three segments.
1) Optimize the second sip of tracer 1 to prevent a significant effect of a high concentration of analyte 1 on the detection of analyte 2.
2) Optimize the second sip of tracer 2 to prevent a significant effect of a high concentration of analyte 2 on the detection of analyte 3.
3) Optimize the third sip of tracer 1 to prevent a significant effect of a high concentration of analyte 1 on the detection of analyte 3.

The optimization is done by varying the amount of the sip in question and monitoring the difference in the mP readings of the subsequent stage for a sample containing none of the analyte for the tracer in optimization and for a sample containing a very high concentration of that analyte. The tables below are comprised of the data from the actual runs in the three segments of the optimization of an assay.

Optimize $T_1$ 2nd Sip

| 2nd Sip vol | Phencyclidine mP | | mP diff*** |
|---|---|---|---|
| | NHU* | Barb Stock** | |
| 1.0 | 163.17 | 174.92 | 11.75 |
| 1.5 | 166.37 | 176.28 | 9.91 |
| 1.6 | 163.14 | 174.34 | 11.20 |
| 1.7 | 167.11 | 174.33 | 7.22 |
| 1.8 | 169.76 | 173.32 | 3.56 |
| 1.9 | 162.34 | 172.50 | 10.16 |
| 2.0 | 161.25 | 165.48 | 4.24 |
| 2.1 | 164.91 | 161.28 | −3.63 ← |
| 4.0 | 170.66 | 148.60 | −22.06 |

*Normal Human Urine
**Secobarbital @ 1000 mg/ml
***mPNHU minus mP Barb Stock
← = optimum sip volume Optimize $T_2$ 2nd Sip

| Sip vol | Opiates mP | | mP diff |
|---|---|---|---|
| | NHU | Barb stock* | |
| 1.0 | 292.98 | 317.95 | 24.97 |
| 1.9 | 281.24 | 281.79 | 0.55 ← |
| 2.0 | 278.37 | 275.83 | −2.54 |
| 2.1 | 279.42 | 271.30 | −8.12 |

*Phencyclidine @ 300 mg/ml
← = optimum sip volume

Optimize $T_1$ 3rd Sip

| Sip vol | Opiates mP | | mP diff |
|---|---|---|---|
| | NHU | Barb stock | |
| 4.9 | 275.96 | 309.49 | 33.53 |
| 6.0 | 275.81 | 277.39 | 1.59 ← |
| 6.1 | 280.44 | 277.21 | −3.23 |
| 7.4 | 264.68 | 240.52 | −24.16 |

Based on the results of this testing the volumes of the tracer sips chosen for this particular set of reagents were as follows:

| | Volumes Chosen (microliters) | | |
|---|---|---|---|
| | $T_1$ | $T_2$ | $T_3$ |
| 1st | 25 | 25 | 25 |
| 2nd | 2.1 | 1.9 | — |
| 3rd | 6.0 | — | — |

Using these volumes, runs were performed with various samples and the following results were obtained, demonstrating, in actual runs, the lack of effect of the concentration of one analyte on the detection of another.

| Sample | mP | | |
|---|---|---|---|
| | Barb | PCP | Opts |
| NHU | 229.95 | 161.99 | 286.11 |
| High Barb | 59.88 | 159.56 | 287.38 |
| High PCP | 232.08 | 40.51 | 287.84 |

EXAMPLE VI

EXAMPLE OF THE COMBINATION TECHNOLOGY ON ANALYTES OTHER THAN ABUSED DRUGS

Following are date tables containing runs in the Combination format utilizing reagents from two assays currently running on the TDx ® instrument. The assays are for the cardiac antiarrhythmic drug procainamide and its major metabolite N-Acetylprocainamide (NAPA). The reagents used are as designated below. The S-pot (antiserum rgt) was composed of a 50/50 mix of the S reagents from the two kits. The tracers were used in full strength as $T_1$ and $T_2$. The P-pot reagent from the procainamide kit was used in this experiment.

The runs were accomplished by using the pipetting sequence currently utilized for the BPO assay, substituting the reagents as described above. The $T_3$ reagent pot was filled with TDx ® Dilution Buffer since only two active reagent systems were involved in these runs. The first stage is the procainamide reading and the second stage is the NAPA reading.

Run #1 was a run with the procainamide calibrators and controls, and run #2 was with the NAPA calibrators and controls. In Run #1 the downward trend as expected occurred for the calibrators in the mP 1 column. The slight upward trend in the mP 2 column (NAPA mP) is due to the nonoptimal settings of the $T_1$ second sip, as noted before in explanation of the BPO assay optimization. In Run #2, the downward trend is seen in the NAPA mp 2 column. The slight downward trend in the mP 1 column is due to a slight cross-reactivity of the procainamide antiserum with the NAPA molecule. This points out a need for no, or very minimal, cross-reactivities of the antibodies used in Combination Assays.

Also included in the data tables, is the output from a computer curvefitting program showing good curve-fits for both assays as evidenced by the controls reading close to their respective targets when read back from the fit curve. This demonstrates the selectivity of the Combination technology in this application.

| Sample | mP 1 | mP 2 | Concentrations | |
|---|---|---|---|---|
| | | | Target | Actual* |
| | | RUN #1 | | |

-continued

| Sample | mP 1 | mP 2 | Concentrations Target | Actual* |
|---|---|---|---|---|
| Procainamide A Cal | 251.64 | 227.45 | | |
| Procainamide B Cal | 157.08 | 255.94 | | |
| Procainamide C Cal | 119.45 | 263.23 | | |
| Procainamide D Cal | 99.54 | 265.29 | | |
| Procainamide E Cal | 79.20 | 268.49 | | |
| Procainamide F Cal | 67.41 | 266.76 | | |
| Low Control | 130.64 | 257.98 | 2.0 | 1.93 |
| Med Control | 90.09 | 266.03 | 6.0 | 6.56 |
| High Control | 75.51 | 265.11 | 15.0 | 12.39 |
| RUN #2 | | | | |
| NAPA A Cal | 251.58 | 225.27 | | |
| NAPA B Cal | 249.08 | 129.92 | | |
| NAPA C Cal | 240.66 | 78.64 | | |
| NAPA D Cal | 228.93 | 60.31 | | |
| NAPA E Cal | 221.60 | 52.47 | | |
| NAPA F Cal | 206.46 | 47.23 | | |
| Low Control | 242.01 | 95.94 | 4.0 | 3.93 |
| Med Control | 237.26 | 64.42 | 9.0 | 9.74 |
| High Control | 211.12 | 48.80 | 25.0 | 25.27 |

*As calculated from the calibrator mP by a computer curve fitting/interpolation program The Procainamide reagents consist of the following:
P Pretreatment Solution. Surfactant in buffer with protein stabilizer.
  Preservative: 0.1% Sodium Azide.
S Antisera. Procainamide Antiserum (Rabbit) in buffer with protein stabilizer.
  Preservative: 0.1% Sodium Azide.
T Tracer. Procainamide—fluorescein tracer in buffer with surfactant and protein stabilizer.
  Preservative: 0.1% Sodium Azide.

The N-Acetylprocainamide reagents consist of the following:
P Pretreatment Solution. Surfactant in buffer containing protein stabilizer.
  Preservative: 0.1% Sodium Azide.
S Antisera. N-acetylprocainamide Antiserum (Sheep) in buffer with protein stabilizer.
  Preservative: 0.1% Sodium Azide.
T Tracer. N-acetylprocainamide—fluorescein tracer in buffer containing surfactant and protein stabilizer.
  Preservative: 0.1% Sodium Azide.

Those skilled in the art will recognize or be able to ascertain, using no more than routine experimentation, many equivalents to the specific embodiments of the invention described herein. Such equivalents are intended to be encompassed within the scope of this invention.

I claim:

1. A method for performing multiple fluorescence polarization immunoassays of a biological fluid sample contained in a single container wherein the presence of specific analytes ($A_n$) where n is an integer of 2 or greater, and their respective quantitative amounts are determined, comprising:
   (a) contacting the sample and a combination of at least two antiserum reagents ($S_n$ wherein n is an integer of 2 or greater) from at least two or more assays, incubating the resultant mixture of $A_n$ and $S_n$ to an equilibrium state;
   (b) taking a fluorescence reading, recording said reading as a blank reading $B_1$;
   (c) adding a tracer $T_1$ and incubating the mixture of $A_n$, $S_n$ and $T_1$ to an equilibrium state;
   (d) taking a fluorescence reading $R_1$, recording said reading $R_1$ as $B_2$;
   (e) adjusting the $R_1$ reading by subtraction of $B_1$ and calculating a mP value; and
   (f) repeating at least once steps (c), (d) and (e) using $T_2$, $B_2$ and sequentially $T_{2+m}$ and $B_{2+m}$ wherein m is an integer of 1 or greater.

2. A method according to claim 1 wherein the multiple fluorescence polarization immunoassays of a single biological fluid sample is directed to detection and quantification of abuse drugs selected from the group consisting of morphine, heroin, hydromorphone, oxymorphone, codeine, hydrocodone, dextromethorphan, cannabinoids, barbiturates, phenycyclidine and their respective metabolites.

3. The method according to claim 1 wherein the multiple fluorescence polarization immunoassays of a single biological fluid sample is directed to detection and quantification of abuse drugs selected from the group consisting of cocaine, cannabinoids, amphetamines, methamphetamines and their respective metabolites.

4. The method according to claim 1 wherein the multiple fluorescence polarization immunoassays of a single biological fluid sample is directed to detection and quantification of abuse drugs selected from the group consisting of opiates, phencyclidine, barbiturates and their respective metabolites.

5. The method according to claim 1 wherein the multiple fluorescence polarization immunoassays of a single biological fluid sample is directed to detection and quantification of therapeutic drugs selected from the group consisting of steroids, antiasthmatic drugs, antineoplastic drugs, antiarrhythmic drugs, anticonvulsant drugs, antibiotics, antiarthritic drugs, antidepressant drugs and their respective metabolites.

6. A method for performing multiple fluorescence polarization immunoassays of a biological fluid sample contained in a single container wherein the presence of specific analytes ($A_n$) where n is an integer of 2 or greater, and their respective quantitative amounts are determined, comprising:
   (a) contacting the sample and a combination of at least two antiserum reagents ($S_n$ wherein n is an integer of 2 or greater) from at least two or more assays, incubating the resultant mixture of $A_n$ and $S_n$ to an equilibrium state;
   (b) taking a fluorescence reading, recording said reading as a blank reading $B_1$;
   (c) adding a tracer $T_1$ and incubating the mixture of $A_n$, $S_n$ and $T_1$ to an equilibrium state;
   (d) taking a fluorescence reading $R_1$, recording said reading $R_1$ as $B_2$;
   (e) adjusting the $R_1$ reading by subtraction of $B_1$ and calculating a mP value; and
   (f) repeating at least once steps (c), (d) and (e) using $T_2$, $B_2$ and sequentially $T_{2+m}$ and $B_{2+m}$ wherein m is an integer of 1 or greater; and
   (g) maintaining concentration of each antiserum reagent $S_n$ and tracer $T_n$ wherein n is an integer of one or greater by addition of $S_n$ and $T_n$ after each mP calculation.

7. A method according to claim 6 wherein the multiple fluorescence polarization immunoassays of a single biological fluid sample is directed to detection and quantification of abuse drugs selected from the group consisting of morphine, heroin, hydromorphone, oxymorphone, codeine, hydrocodone, dextromethorphan, cannabinoids, barbiturates, phenycyclidine and their respective metabolites.

8. The method according to claim 6 wherein the multiple fluorescence polarization immunoassays of a single biological fluid sample is directed to detection and quantification of abuse drugs selected from the group consisting of cocaine, cannabinoids, amphetamines, methamphetamines and their respective metabolites.

9. The method according to claim 6 wherein the multiple fluorescence polarization immunoassays of a single biological fluid sample is directed to detection and quantification of abuse drugs selected from the group consisting of opiates, phencyclidine, barbiturates and their respective metabolites.

10. The method according to claim 6 wherein the multiple fluorescence polarization immunoassays of a single biological fluid sample is directed to detection and quantification of therapeutic drugs selected from the group consisting of steroids, antiasthmatic drugs, antineoplastic drugs, antiarrhythmic drugs, anticonvulsant drugs, antibiotics, antiarthritic drugs, antidepressant drugs and their respective metabolites.

11. The method according to claim 6 wherein step (g) is carried out by altering the amount of $T_n$ addition added in subsequent steps to modulate the reactions relative to incomplete equilibrium caused by equilibrium interference due to analyte $A_n$ concentration peak.

* * * * *